United States Patent [19]

Wetterlin et al.

[11] Patent Number: 4,907,583
[45] Date of Patent: Mar. 13, 1990

[54] DEVICE IN POWDER INHALATORS

[75] Inventors: Kjell I. L. Wetterlin, S Sandby, Sweden; Risto Virtanen, Nurmijärvi, Finland; Jan A. R. Andersson, S Sandby, Sweden

[73] Assignee: Aktiebolaget Draco, Lund, Sweden

[21] Appl. No.: 287,611

[22] Filed: Dec. 16, 1988

Related U.S. Application Data

[63] Continuation of Ser. No. 19,057, Feb. 26, 1987, abandoned.

[30] Foreign Application Priority Data

Mar. 7, 1986 [SE] Sweden .................... 86010600

[51] Int. Cl.⁴ .................... A61M 15/00
[52] U.S. Cl. .................... 128/203.15; 128/203.12; 128/200.18
[58] Field of Search .................... 128/200.18, 200.21, 128/203.12, 203.15, 203.22–203.24, 204.13; 239/461, 467, 487, 489, 500–501, 518–519; 222/345, 349

[56] References Cited

U.S. PATENT DOCUMENTS

| | | | |
|---|---|---|---|
| 1,309,597 | 7/1919 | Parker | 239/489 |
| 1,431,177 | 10/1922 | Palmer | 128/203.22 |
| 2,604,094 | 7/1952 | Miller et al. | 128/203.15 |
| 2,674,999 | 4/1954 | Cox . | |
| 2,804,341 | 8/1957 | Bete | 239/501 |
| 4,014,470 | 3/1977 | Burnham | 239/487 X |
| 4,147,166 | 4/1979 | Hansen | 128/203.15 |
| 4,353,365 | 10/1982 | Hallworth et al. | 128/203.15 |
| 4,446,862 | 5/1984 | Baum et al. | 128/203.15 |
| 4,524,769 | 6/1985 | Wetterlin | 128/203.15 |
| 4,570,630 | 2/1986 | Elliott et al. | 128/203.15 |

FOREIGN PATENT DOCUMENTS 2152819 8/1985 United Kingdom .......... 128/203.15

Primary Examiner—Angela D. Sykes
Attorney, Agent, or Firm—White & Case

[57] ABSTRACT

Device in a previously known powder inhalator intended for inhalation of an air flow which contains pharmacologically active compound in micronized form. The powder inhalator comprises a nozzle unit (2) with a nozzle aperture (2a) as well as a container unit (3) with a releasing or dosing unit (6) for delivering the active compound. The air flow generated by inhalation is at least partly aspirated through an air conduit (7) located in the container unit (3), which conduit extends from an air inlet (8), communicating with the environment, via said releasing or dosing unit (6), up to said nozzle unit (2). According to the invention, deflector devices are stationarily arranged in the container unit (3) and/or in the nozzle unit (2), said deflector devices, for example in the shape of a helical channel portion (13), being arranged to create a powerful deflecting movement for the purpose of disrupting said powder particles into the respirable particle size distribution (less than 5 μm).

10 Claims, 5 Drawing Sheets

DEVICE IN POWDER INHALATORS

This application is a continuation of application Ser. No 019,057 filed on Feb. 26, 1987, now abandoned.

BACKGROUND OF THE INVENTION

The present invention relates to a device in powdered inhalators intended to be used for local administration of drugs to the respiratory tract and lungs of a patient.

There are different types of powder inhalators, for example those which operate with hard gelatin capsules from which the pharmacologically active compound is released during inhalation through the inhalator, and those which dose the pharmacologically active compound directly into the air conduit by means of a special dosing unit, said compound being administered to patients during inhalation through the inhalator. All substances which are used in such inhalators are atomized or micronized so that the main fraction of the substance is within the particle size range which is termed the respirable range, that is, particles smaller than 5 $\mu$m. This applies both to inhalators operating with pure active compound and to those where the active compound is mixed with suitable diluting agents such as lactose, sucrose etc. The active compound is enclosed, without carrier substance or when appropriate together with carrier substance, in hard gelatine capsules or directly in a storage unit in the inhalator, which storage unit is connected to a suitable dosing unit incorporated in the powder inhalator. When the substance is to be released from the hard gelatine capsule or from the dosing unit into the air conduit of the powder inhalator, it is essential that the largest possible quantity of primary particles is obtained in the respirable range, that is, smaller than 5 $\mu$m, at flows which can be generated by a patient suffering from disease of the respiratory tract. A sufficient quantity of particles smaller than 5 $\mu$m can be obtained to achieve a therapeutic effect by means of a particle disintegrating construction according to US-A-4 524 769, in which a constriction in the nozzle unit increases the flow velocity of the inhalation air and a propeller contributes to an increase in the quantity of particles in the respirable range. This construction implies, however, that movable parts are used in the nozzle unit.

SUMMARY OF THE INVENTION

The object of the invention is to accomplish, against this background, a device in powder inhalators of the known kind which is stated in the preamble of claim 1, in such way that during inhalation and without the help of movable parts an effective disintegration of powder aggregates into particles within the respirable range is achieved.

This object is attained according to the invention by deflector devices stationarily arranged in the container and/or nozzle unit, which deflector devices are arranged to create a powerful deflecting movement, preferably a rotary movement, for example through the deflector devices comprising one or more helical channel portions.

During the deflection the particles will on the one hand be dashed against the walls of the deflector devices by centrifugal force, whereby large particles or particle aggregates are ground into small particles, and on the other hand collide with each other which results in a mutual grinding action between the particles. The overall result is in that a great quantity of particles can be generated within the respiratory range.

The deflector devices can be arranged in many different ways, in particular in the form of helical channel portions, as will be evident from the claims and the detailed description below.

The invention is described in greater detail below with reference to the accompanying drawings which illustrate some working examples.

DESCRIPTION OF EMBODIMENTS

Figure 1:
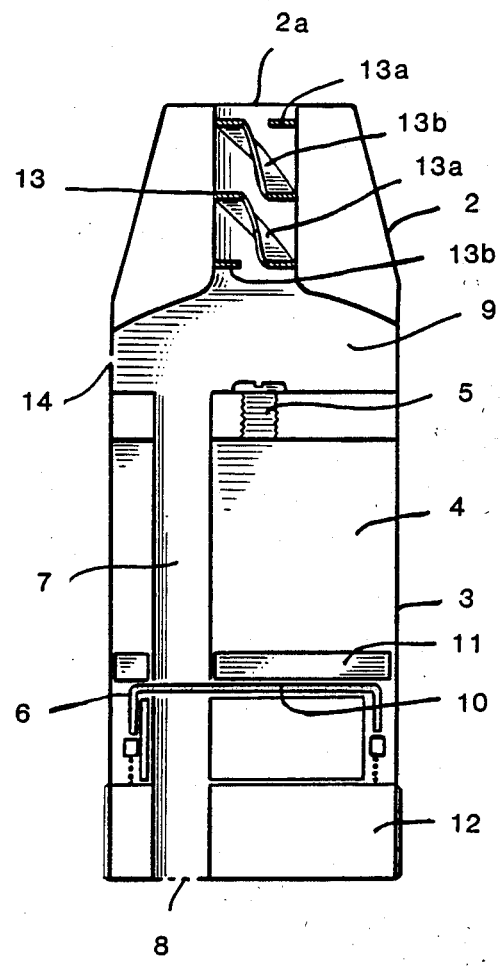
FIG. 1 shows axial cross-section through first embodiment of device according to the invention with a helical channel portion in the nozzle unit of the powder inhalator.
Figure 2:
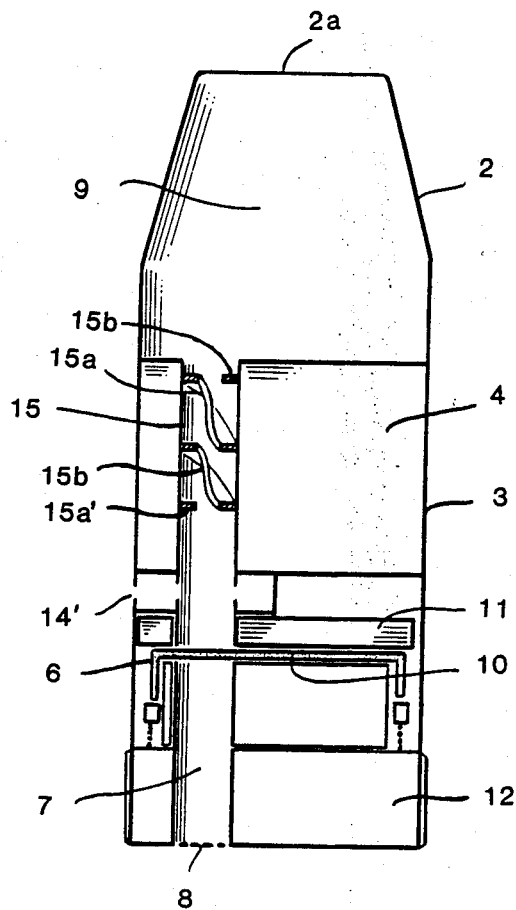
FIG. 2 shows a corresponding view of a second embodiment with a helical channel portion in the container unit of the powder inhalator.
Figure 3:
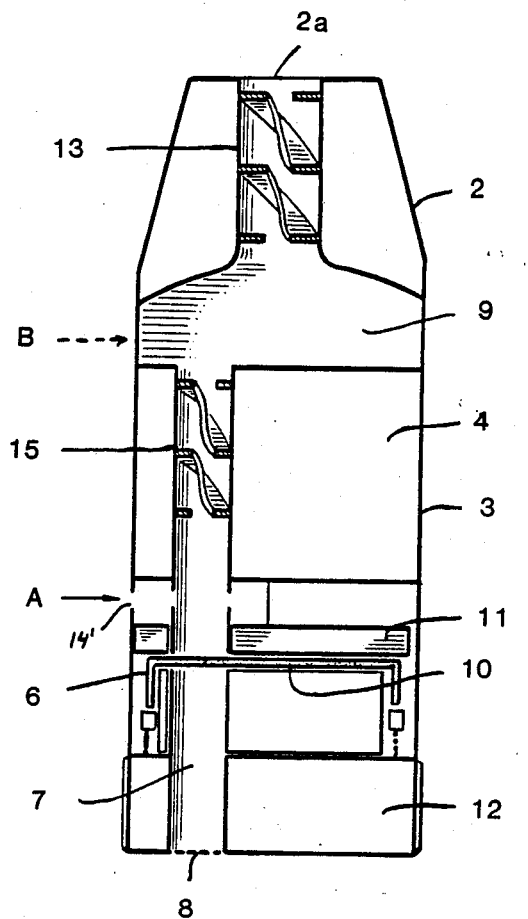
FIG. 3 shows a corresponding view of a third embodiment with a helical channel portion in both the nozzle and the container unit.
Figure 4:
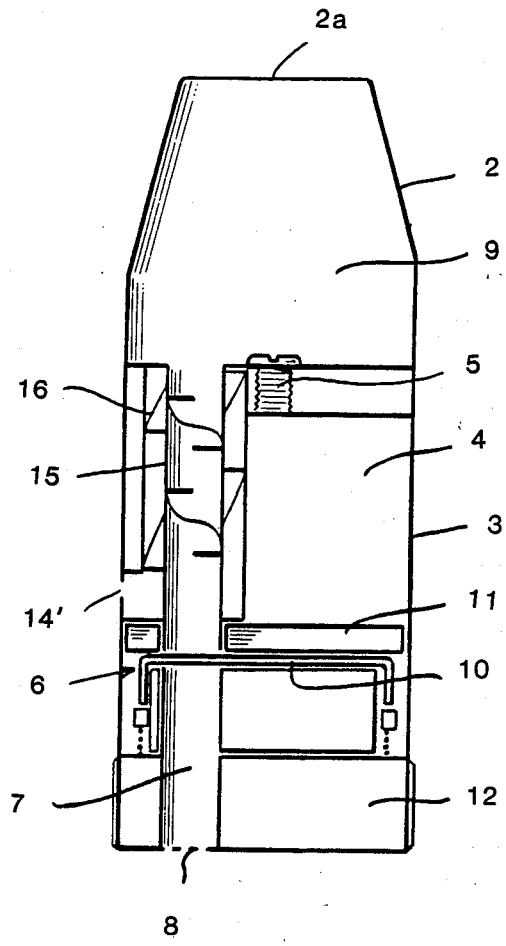
FIG. 4 shows a corresponding view of a fourth embodiment with double helical channel portions in the container unit.
Figure 5:
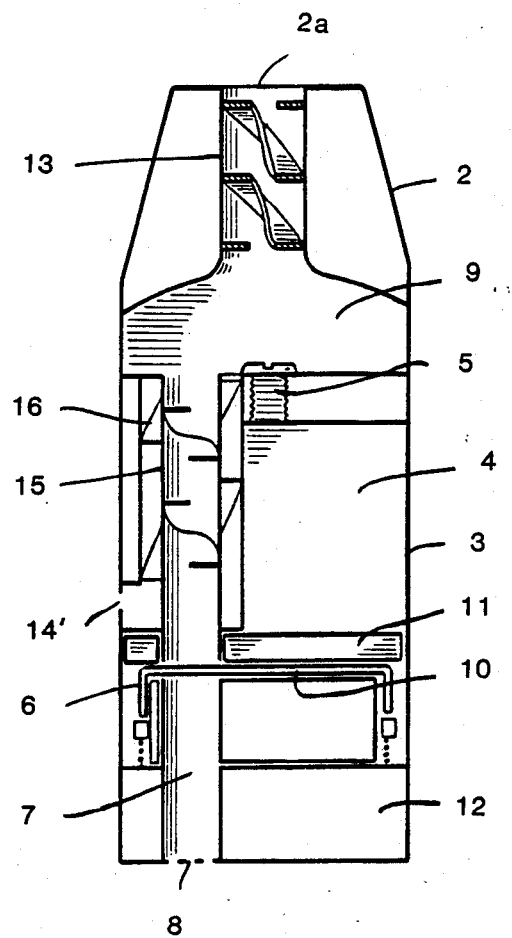
FIG. 5 shows a corresponding view of a fifth embodiment with double helical channel portions in the container unit and with a helical channel portion in the nozzle unit.

The powder inhalators illustrated in FIGS. 1–5 are all of a known type (see U.S. Pat. No. 4,524,769), named dosage inhalators, and comprise a nozzle unit 2 with a nozzle aperture 2a located at the top and a container unit 3 with a storage chamber 4 for the active compound (which can be refilled through an upper opening sealed by a plug 5—shown in FIGS. 1, 4 and 5 only) and a dosing unit 6 for delivering a dose of the active compound to an air conduit 7. This air conduit 7 extends from a lower air inlet 8, past the dosing unit 6, where the active compound is emitted to the air flow generated by inhalation, and ends in the lower part of the nozzle unit 2, which consists of a free internal chamber 9 (in the embodiments according to FIGS. 2 and 4 the chamber 9 occupies the whole space inside the nozzle unit 2).

The likewise known dosing unit 6 comprises essentially a perforated membrane 10 in the form of a plane, rotary membrane whose perforations in connection with the storage chamber 4 are filled with powder substance by means of resilient scrapers 11 and which in the area of the air conduit 7 emits the powder substance under the action of the air flow generated by inhalation passing through the perforations of the membrane. The dosing unit 6 is operated by an outer, somewhat knurled grip collar 12, which is connected to the rotary membrane 10 so as to transmit the rotary movement. Thus the dosing is achieved by rotating the membrane 10 a fixed distance by means of the grip collar 12.

According to the present invention deflector devices are arranged in the nozzle unit 2 and/or the container unit 3 and are adapted to powerfully deflect the powder-saturated air flow generated by inhalation. In the illustrated embodiments the deflector devices comprise helical channel portions which give the air flow a rotating, helical pattern of motion. The deflector devices are intended to disrupt aggregated particles by means of the centrifugal force generated when the inhalation air flows through the region of the deflector devices. As discussed above, an effective grinding is accomplished, partly by the particles impacting on the deflecting wall surfaces, partly by mutual collisions between the particles. To attain a sufficient rotary motion of the air flow, it is essential that the radial extension of the hollow space in the cross-section area of the nozzle unit 2 is small compared to the radial extension of the deflector devices. Furthermore, the air flow is additionally accelerated by the fact of the nozzle unit 2 being shaped with a constricted cross-section in the region of the deflector devices.

According to FIG. 1 a helical channel portion 13 as described above is arranged at the top of the nozzle unit 2 adjacent the nozzle aperture 2a. The helical channel portion 13, which can be arranged in a detachable liner body in the nozzle unit 2, comprises two interacting helical channel walls 13a and 13b, mutually displaced half a revolution. Furthermore, along the centre line of the helical channel walls there is formed a small, straight hollow space which reduces the flow resistance, at least initially, but which only conducts a small part of the total flow. Consequently air is aspirated into the air intake 8 and the air flow entrains the substance particles in the dosing unit 6, whereupon the particle-saturated air flow enters the chamber 9 of the nozzle unit, where it is mixed with dilution air aspirated through one or more separate air inlets 14 in the side walls of the nozzle unit 2 close to the top end of the container unit 3. Subsequently the composite, particle-saturated air flow is constrained to follow a helical path along the respective helical channel walls 13*a*, 13*b* until it leaves the nozzle aperture *2a*.

In the embodiment according to FIG. 2 the flow proceeds quite freely in the internal chamber 9 of the nozzle unit 2, but the air flow has already been set in helical rotation in the upper part of the air conduit 7 by passing through a similar helical channel portion 15 with helical channel walls 15*a*, 15*b* mutually displaced half a revolution. In this case dilution air is aspirated through one or more air inlets 14' located in the central part of the container unit 3 somewhat above the dosing unit 6, that is, the dilution should take place before the air flow is set in powerful rotation. The rotary movement will continue as a turbulent flow for at least a short distance up the nozzle unit 2 before the air flow leaves the aperture *2a*.

The embodiment according to FIG. 3 constitutes essentially a combination of FIGS. 1 and 2, that is, a helical portion 13 or 15 is arranged both in the upper part of the nozzle unit and in the upper part of the air conduit 7, said dilution air inlets being located either as in FIG. 1 (broken arrow B) or as in FIG. 2 (arrow A). The directions of rotation according to FIG. 3 are the same in both helical channel portions 13, 15, and consequently they cooperate with each other to achieve a higher rotary speed. In principle it is possible to join the two portions together to form a long continuous helical channel portion. As an alternative, it is possible for the two helical channel portions 13, 15 to have opposite directions of rotation, whereby one deliberately aims to generate a turbulent flow in the chamber 9, with the air flow reversing its direction of rotation. Such turbulent flow can also accomplish effective disintegration of aggregates by frequent mutual collisions.

In the embodiments according to FIGS. 4 and 5 the dilution air is aspirated from an air inlet 14' (located somewhat above the dosing unit 6, as in FIG. 2) via an envelope surface 16 with helical channel walls surrounding the upper part of the air conduit 7. Consequently the particle-saturated air flow and the dilution air flow enter the chamber 9 separately, although both air streams are set in rotation (in the same or opposite directions). In the embodiment according to FIG. 5 an additional rotary motion is achieved in the helical channel portion 13 of the nozzle unit 2. In principle it is conceivable to omit the helical channel portion 15 in the upper part of the air conduit 7 in the embodiments according to FIGS. 4 and 5, in which case the rotary motion of the dilution air will act on the particle-saturated air flow in the chamber 9. It is also possible to have the helical channel portion in the envelope surface 16 end in the upper part of the air conduit 7.

Besides the above-mentioned effects of the collisions of the particles and aggregates with the channel walls and with other particles and aggregates, the different helical channel portions 13, 15, 16 (in FIGS. 1–5) create a constricting effect which increases the flow velocity and thereby further promotes disintegration. However, the constricting effect, that is, the cross-section area of the helical channel portions, must be adjusted to avoid making the inhalation resistance too great for patients with disease of the respiratory tract, such as asthmatics. In general the total cross-section area can be varied between 5 and 50 $mm^2$, while the overall length of the helical channel portions can amount to 5–50 mm.

The ratio between the radial extension of the deflector devices and the radial extension of the central hollow space is an essential factor for the efficient disintegration of powder aggregate into particles in the respirable range, that is, the cross-section area of said hollow space must be adjusted to avoid too much of the particle-saturated air flow to pass through the hollow space and cause an inefficient disintegration. Consequently, it is possible to omit the central hollow space to further promote disintegration. The illustrated embodiments show deflector devices in which the radial extension of the hollow space is about 10–20 of the radial extension of the deflector devices, as appears from FIGS. 1–5. In a cross-section in the region of the deflector devices the ratio of the radial extension of the central hollow space to that of the deflector devices can be varied essentially between 0–50% to attain efficient disintegration and also to provide an inhalation resistance which is not too great for patients suffering from disease of the respiratory tract. In the embodiments according to FIGS. 1, 3 and 5 the constricted cross-section in the nozzle unit 2 causes an increased acceleration of the particle-saturated air flow and hence a more efficient disintegration.

The invention is applicable in many ways within the scope of the claims. Thus the deflector devices can be placed in different types of powder inhalators (according to the preamble of claim 1), and further the deflector devices can be designed in other ways than in the embodiments. In the first place they do not need to generate specifically a rotary or helical flow, but other powerful deflected flow paths are also possible, such, as labyrinthine or meandering flow path. Likewise the channel walls do not have to form continuous guiding surfaces but can consist of a plurality of consecutively arranged, complementary guiding surfaces in the shape of plates or bodies with slightly curved surfaces which together accomplish a powerful deflection of the air flow.

We claim:

1. In a powder inhalator for inhalation of an air flow generated at inhalation having a container containing a pharmacologically active compound in atomized or micronized form, a conduit extending through the container and having an air inlet, means for delivering a dose of the compound to the conduit, an outlet from the conduit for outflow of the compound in an air flow admitted at least partly through the air inlet, and a nozzle having a nozzle aperture and communicating with the conduit outlet, the conduit and nozzle together forming a channel for delivery of the compound upon inhalation, the improvement comprising deflector means in the channel for imparting a strong deflecting and accelerating movement to the flow of air and compound through the channel relative to the axis of the channel, wherein the deflector means are stationarily affixed in the channel along at least one section thereof between the dose delivery means and the nozzle aperture, the deflector means having at least a substantial radial extent towards the axis of the channel such that the radial extent of any open space along the axis of the channel adjacent the deflector means is small compared to the radial extents of the deflector means, the deflector means thereby acting to promote disintegration of powder aggregations into particles within the respirable range by causing collisions of such aggregations with the deflector means and with each other.

2. The improvement according to claim 1, wherein the deflector means comprise deflector elements shaped and positioned to deflect the flow of air and compound rotationally with respect to the axis of the channel.

3. The improvement according to claim 2 wherein there is an open space along the axis of the channel adjacent the deflector means to lower the resistance to the flow of the air and compound.

4. The improvement according to claim 3 wherein the ratio of the radial extent of the open space to the radial extent of the deflector means is not greater than one to two.

5. The improvement according to claim 2 wherein the deflector means are shaped to define at least one helical portion along said section of the channel.

6. The improvement according to claim 5 wherein said section is in the nozzle adjacent the nozzle aperture.

7. The improvement according to claim 6 wherein a portion of the nozzle upstream from said section, relative to the direction of flow of air and compound through the channel, has a continuous diminishing cross-sectional area so as to increase the velocity of the flow of air and compound.

8. The improvement according to claim 5 wherein said section is located in the conduit between the dose delivery means and the conduit outlet.

9. The improvement according to claim 5 wherein the cross-sectional area of the helical portion is between five square millimeters and fifty square millimeters and the length of said portion is between five millimeters and fifty millimeters.

10. The improvement according to claim 4 wherein there is at least one air inlet to the channel between the dose delivery means and the nozzle for aspiration of dilution air into the flow of air and compound.

* * * * *